(12) United States Patent
Schmitt

(10) Patent No.: US 10,614,245 B2
(45) Date of Patent: *Apr. 7, 2020

(54) METHOD AND SYSTEM FOR PROTECTING PATIENT INFORMATION ON MEDICAL PRESCRIPTION LABELS

(71) Applicant: Nathan David Schmitt, Cascade, IA (US)

(72) Inventor: Nathan David Schmitt, Cascade, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/410,071

(22) Filed: May 13, 2019

(65) Prior Publication Data

US 2019/0266349 A1  Aug. 29, 2019

Related U.S. Application Data

(63) Continuation of application No. 16/108,997, filed on Aug. 22, 2018, now Pat. No. 10,331,905.

(60) Provisional application No. 62/717,930, filed on Aug. 13, 2018, provisional application No. 62/549,369, filed on Aug. 23, 2017.

(51) Int. Cl.
*G06F 21/62* (2013.01)
*G16H 10/60* (2018.01)
*G16H 20/13* (2018.01)

(52) U.S. Cl.
CPC ......... *G06F 21/6245* (2013.01); *G16H 10/60* (2018.01); *G16H 20/13* (2018.01); *G06F 21/6272* (2013.01)

(58) Field of Classification Search
CPC .. G09F 3/10; G09F 3/0292; G09F 2003/0213; G09F 2003/0272
See application file for complete search history.

(56) References Cited

U.S. PATENT DOCUMENTS

| | | | | |
|---|---|---|---|---|
| 5,775,735 A | * | 7/1998 | Bolnick | G09F 3/10 283/101 |
| 2003/0006606 A1 | * | 1/2003 | Franko, Sr. | G09F 3/10 283/81 |
| 2005/0258636 A1 | * | 11/2005 | Bova | G09F 3/005 283/81 |
| 2007/0029787 A1 | * | 2/2007 | Loftin, III | G09F 3/0288 283/74 |
| 2007/0279233 A1 | * | 12/2007 | Ryckman | G06K 19/07758 340/572.8 |

(Continued)

OTHER PUBLICATIONS

Article entitled "How to Dispose of Empty Medication Bottles" from The Trustees of Columbia University in the City of New York—http://goaskalice.columbia.edu/answered-questions/how-dispose-empty-medication-bottles-0.

(Continued)

*Primary Examiner* — Gary C Hoge
(74) *Attorney, Agent, or Firm* — Simmons Perrine Moyer Bergman PLC

(57) ABSTRACT

A system and method for protecting personal information on prescription medicine container labels which includes a label configured for relocating a removable printed label panel to a different location where it bonds over the personal information and thereby uncovering a pre-marked array of fake information intended to mimic authentic information to misdirect and hinder thieves from accessing the authentic personal information.

15 Claims, 4 Drawing Sheets

(56) References Cited

U.S. PATENT DOCUMENTS

| | | | | |
|---|---|---|---|---|
| 2009/0058073 A1* | 3/2009 | George | ............... | G09F 3/0289 283/81 |
| 2011/0155313 A1* | 6/2011 | Black | ............... | B42D 15/025 156/249 |
| 2014/0257843 A1* | 9/2014 | Adler | ............... | G09F 3/0289 705/2 |
| 2016/0055773 A1* | 2/2016 | Barry | ............... | G09F 3/0288 40/638 |

OTHER PUBLICATIONS

LPT Request: Removing Personal Information from Prescription Bottles—Comments in Life Pro Tips at Reddit—htttps://www.reddit.com/r/LifeProTips/comments/2wh4np/lpt_request_removing_personal_information_from/.

ZAP STRIPS Commercial on Vimeo—https://vimeo.com/34738299.

ZAP STRIPS Word Mark Application from US Patent and Trademark Office—http://tsdr.uspto.gov/#caseNumber=85828366&caseSearchType=US_APPLICATION&caseType=DEFAULT&searchType=statusSearch.

* cited by examiner

METHOD AND SYSTEM FOR PROTECTING PATIENT INFORMATION ON MEDICAL PRESCRIPTION LABELS

CROSS REFERENCE TO RELATED APPLICATIONS

This application is a continuation of the non-provisional patent application having Ser. No. 16/108,997 and filed on Aug. 22, 2018, which application claims the benefit of a first provisional application filed on Aug. 23, 2017, and having Ser. No. 62/549,369 entitled "PRESCRIPTION MEDICINE LABEL PROTECTOR," and a second provisional application filed on Aug. 13, 2018, and having Ser. No. 62/717,930 entitled "PRESCRIPTION LABEL PROTECTOR", which are hereby incorporated herein in their entirety by these references.

FIELD OF THE INVENTION

The present invention generally relates to medical prescription labels, and more particularly relates to methods and systems for protecting patient personal information on such labels, and, even more particularly, relates to convenient and effective methods and systems for protecting such information.

BACKGROUND OF THE INVENTION

The field of protection of personal information on prescription containers has seen growth recently. Numerous different variations of methods to protect such information have been implemented.

Some of these methods are commercially available today on Amazon.com and include among others: providing a Miseyo Wide Roller Stamp for imprinting many marks on the label thereby making the original label information difficult to read. Many others on Amazon.com have included label covers with printed information thereon which can be applied over the part of the original label information. However, both of these methods still fall short in convenience, availability and reliability to name a few.

Consequently, there exists a need for improved methods and systems for protecting patient personal information on prescription labels.

SUMMARY OF THE INVENTION

It is an object of one aspect of the present invention to provide a prescription label information protection method which does not, at the time of disposal of the container, require use of additional tools or more materials to be added to the prescription container.

It is a feature of one aspect of the present invention to utilize a dual purpose initially easily removable label portion.

It is an advantage of the present invention to eliminate the need to use any handheld implements to protect information at the time of container disposal.

It is an additional feature of the present invention to provide a method which does not, at the time of disposal of the container, add any new matter to the label.

It is an additional advantage of this embodiment of the present invention to reduce the possibility that a person wanting, at any given time, to protect information on a prescription label will, at such time, fail to possess the necessary materials and/or tools to protect such information.

Accordingly, the present invention is:

A method for protecting patient information on a label of a prescription medication container, comprising the steps of:

providing a label having a first side and an opposing second side;

said first side having a first zone which contains some information and a second zone which is free of any information;

providing a panel which is configured to be relocated from a location above said second zone and placed over said first zone; and relocating said panel and covering from view said some information.

Additionally, the present invention is a system for controlling the display of personal information on prescription labels on prescription containers, the system comprising:

a base layer label configured to be adhered to a container;

said base layer label having a first label portion having a first surface thereon which is configured to receive and retain thereon information;

said base layer label having a second label portion having a second surface which is smoother than said first surface; and a portion adhered to said second surface by an adhesive which is configured to allow said removable portion to be peeled from said second surface with relative ease when compared to a level of effort involved in peeling said removable portion from said first surface after said removable portion has been relocated and adhered to said first surface.

DETAILED DESCRIPTION

Figure 1:
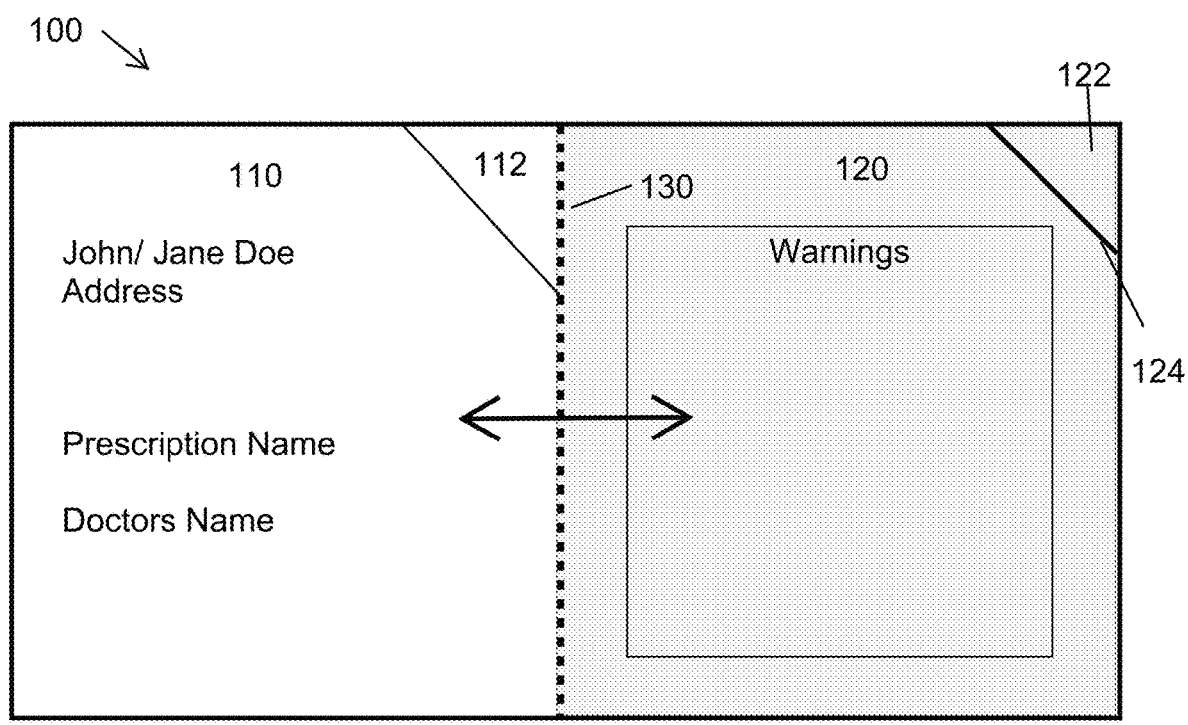
FIG. 1 is view of the label of the present invention, when its parts are configured to permit normal use of a prescription container and to be configured to facilitation protection of information at some future time.

Now referring to the drawings wherein like numerals refer to like matter throughout and more particularly referring to FIG. 1, which is a typical view of a an embodiment of the present invention, during times of normal use of a prescription container. The general concepts of prescription labels with a viewing side with information thereon and a container side with adhesive thereon are known to those skilled in the art. FIG. 1 shows the viewing side of an innovative label of the present invention, generally designated 100, having a fixed label panel 110, which is printed with one of many known printing techniques, such as inkjet, thermal, laser, etching or the like so as to include information about the name and address of the patient, the prescription name and the name of the physician who wrote the prescription. There is a zone 112 in the upper right hand corner of fixed label panel 110 which is clear of any printed matter. Label 100, is an assembly or fabrication of different materials, which as a whole, can be applied to a container as if it were a single piece of material. Label 100 includes a fixed label panel 110, and also is shown including a removable label panel 120 and a perforation line 130, therebetween, or suitable substitute, which permits detachment of removable panel 120. Removable panel 120 is configured to be printed with additional information in a manner similar to the printing on the fixed label panel 110. For example, warnings about the medication or any other information. In the upper right hand corner of removable panel 120 is a removal facilitating region 122 which may be colored and/or labeled with portions of the information protection instructions, such as PEEL HERE.

The removal facilitating region 122, in one embodiment, can be bounded on one side by a perforated line 124 so as to be easily detachable when a force is applied along the perforated line 124, but less so when a perpendicular to perforated line 124 force is applied.

Figure 2:
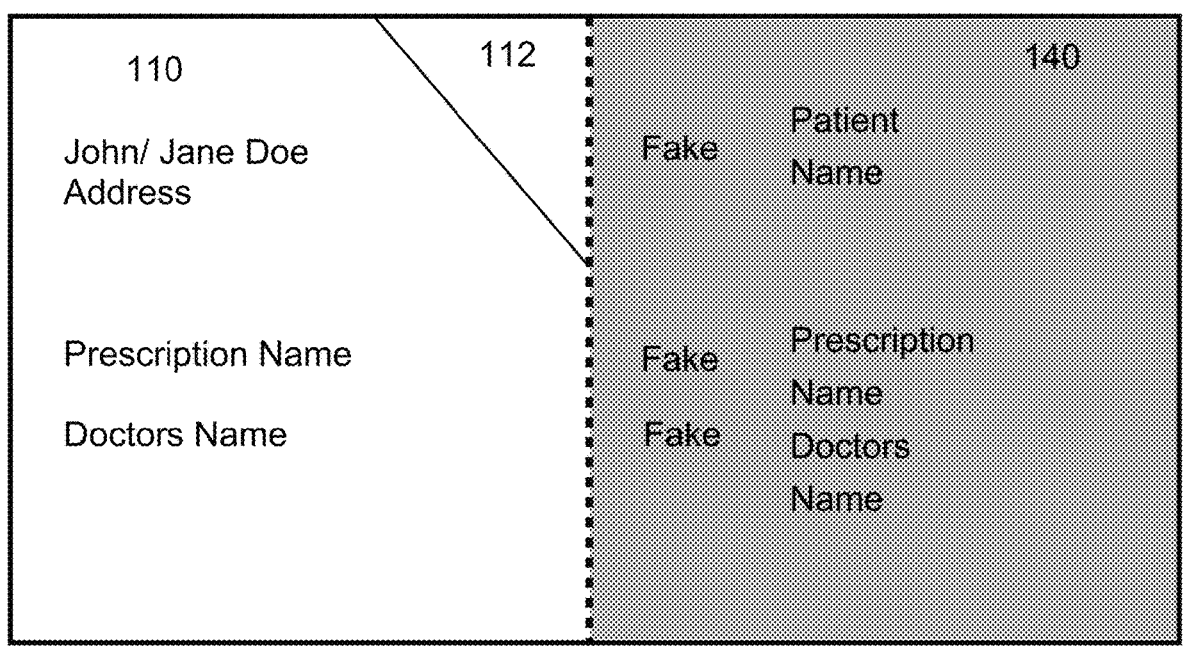
FIG. 2 is a partially transformed configuration of the label of FIG. 1, where a removable panel has been removed from it original location.

Now referring to FIG. 2, there is shown a partially transformed configuration of the label 100 of FIG. 1 where the removable panel 120 has been removed by grasping the removal facilitating region 122 at its most upper right portion and pulling it downward and leftward and generally perpendicular to the perforated line 124. When removable panel 120 is removed, it uncovers a fixed smooth panel 140. In some situations where a thief of personal information may quickly take pictures of containers and then later extract the information from the photos, it may be helpful to have an alternate embodiment of the present invention in which the final protected configuration appears to be a normal unprotected container. The thief may take a quick picture and move on. This can be facilitated by adding fake markings on the fixed smooth panel 140, which are designed to mimic data similar to that which is shown on portions of fixed label panel 110. In low cost embodiments of the present invention, the expense of this fake information could be omitted.

In its original configuration, removable panel 120 is temporarily held in place by an adhesive 401 (FIG. 4) which is chosen to weakly bond to the smooth surface of fixed smooth panel 140 and to bind much more securely to the material on the viewing surface of fixed label panel 110.

Figure 3:
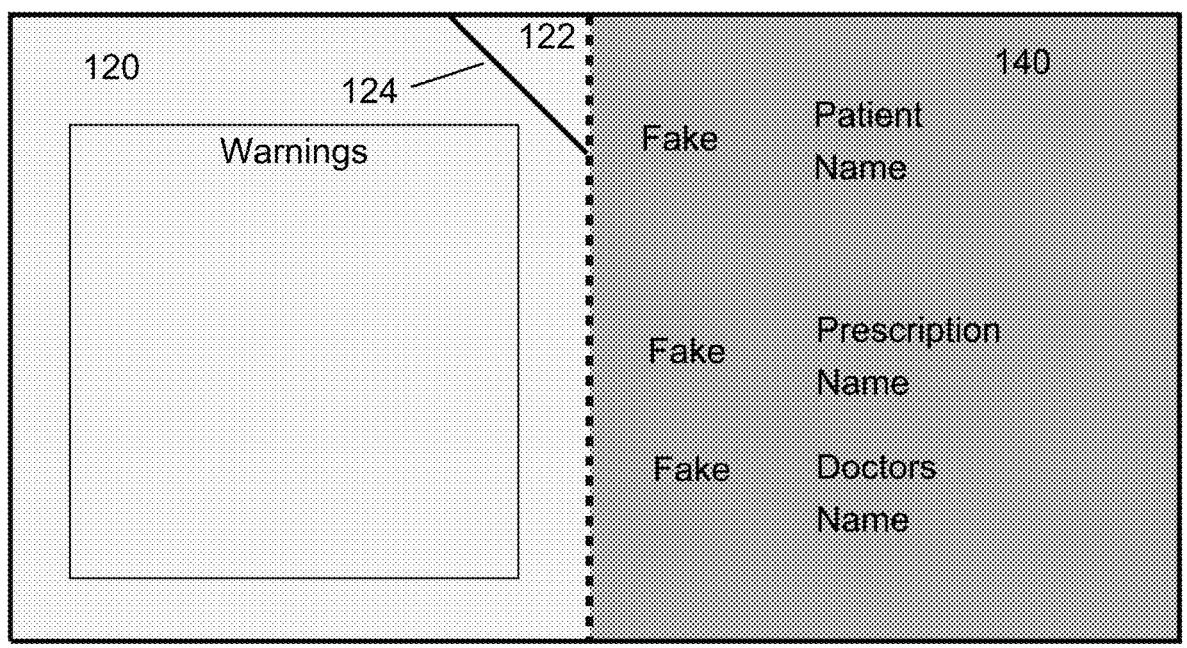
FIG. 3 is a nearly completely transformed configuration of the label of FIG. 1, where the removable panel has been relocated so as to protect information.

Now referring to FIG. 3, there is shown a nearly completely transformed configuration of the label 100 where the removable panel 120 has been placed over the fixed label panel 110, thereby blocking from view the sensitive patient information printed on the surface of fixed label panel 110. The final step of the present method could include the detachment from removable panel 120, of the removal facilitating region 122, by tearing along the perforated line 124. This will make it more difficult for the removable panel 120 to be removed after being adhered to the fixed label panel 110. Once this removal facilitating region 122 is removed, it exposes zone 112 which has been kept free of printed information.

Figure 4:
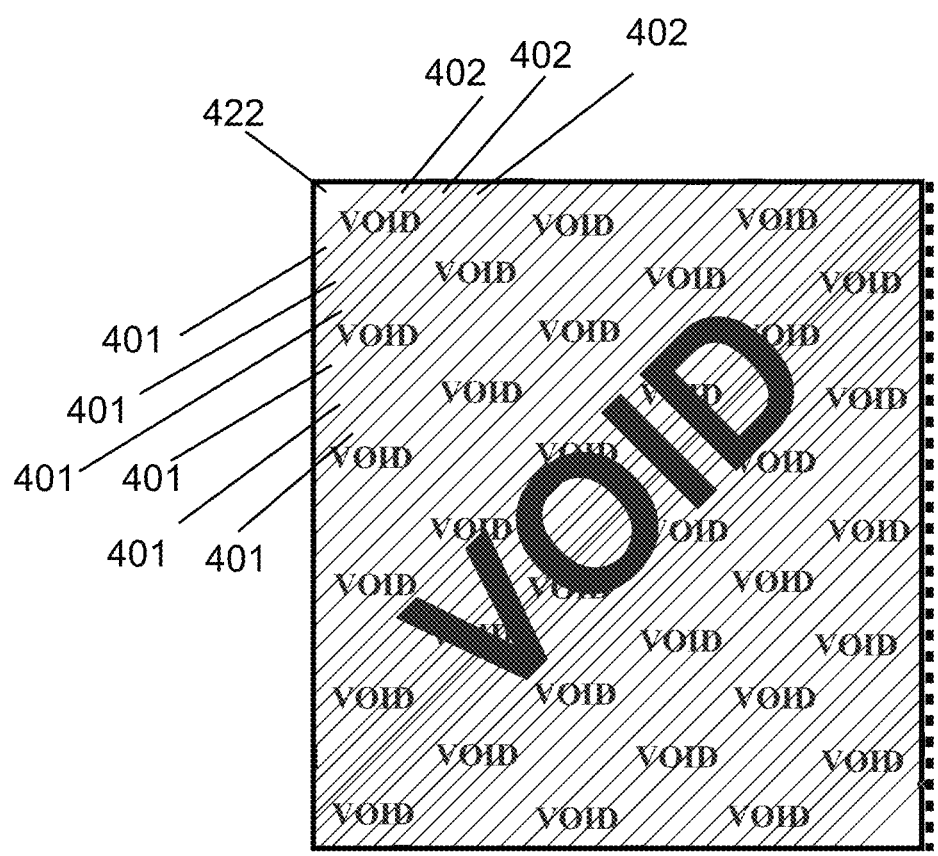
FIG. 4 is a view of an underside of the removable panel of FIGS. 1 and 3.

Now referring to FIG. 4, there is shown an underside of the removable panel 120, which is shown with a zone 422, which is immediately behind the removal facilitating region 122. Zone 422 may be free of any adhesive or it may be attached with a much thicker and much more easily detachable adhesive to facilitate grasping of the same before removal of the removable panel 120. The underside of panel 120 is shown having alternating lines of adhesive 401 and alternating lines 402, which may be one of a solvent or other agent which is selected for its ability to dissolve and/or degrade at least one of: a) the surface of fixed label panel 110 and b) the markings originally printed on the fixed label panel 110. In another embodiment, alternating lines 402 may comprise a material, such as ink, which will tend to bleed onto the fixed label panel 110 (when removable panel 120 is placed over fixed label panel 110, and thereby make it more difficult to read the information originally printed on fixed label panel 110), if a thief were able to separate the removable panel 120 after it has been relocated over the fixed label panel 110.

FIG. 4 also shows the words VOID written across lines 401 and 402. The purpose of this printed matter is to provide a tamper evident configuration which has ink on the surface of fixed label panel 110, if the removable panel 120 is successfully removed after it has been adhered over top of the fixed label panel 110. This could make it easy for personnel to recognize that the patient information has been compromised. In reality, the word VOID as shown in FIG. 4 would not result in the creation of a print of the word VOID on the surface of fixed label panel 110. The arrangement of the ink would instead really need to be a flipped representation of the word VOID. Other flipped variations of words might be preferred. Additionally, there may be text on the face of removable panel 120 saying not to remove the same until the prescription container is emptied and discarded. Also, it might be even better to place the instructions on how to remove the removable panel and relocating it, on the face of fixed label panel 110, so it will not be visible when the protected configuration has been deployed.

Depending upon the manufacturing preferences, the present invention could be manufactured in different ways. The first method of manufacturing the label 100 could be as follows:

1) Provide a single piece of material which will be fixed label panel 110, perforated line 130, and removable panel 120. (This is shown in FIG. 1)
2) Then a smooth plastic layer, which will become fixed smooth panel 140, is attached to the back side of the removable panel 120 by an adhesive which only provides a small amount of holding power.
3) Then a strong adhesive is applied over the back side of fixed label panel 110 and the back side of the smooth plastic layer, which will become the fixed smooth panel 140, and
4) At this point, the label 100 can be attached to a prescription container, or if it is not going to be immediately attached, an easily removable adhesive cover is placed over this adhesive on the back side of the smooth plastic layer.

The second method of manufacture of the present invention (not shown in the figures) could include the following steps:

1) Providing an adhesive backed single base layer with the first end adapted for printing in a manner that is typical to normal labels and the second end being very smooth for allowing easy detachment therefrom of adhesives.
2) Providing a removable panel with an adhesive thereon which is only lightly adhered to the second end, because of the very smooth characteristic of the second end.
3) Said removable panel with the adhesive thereon is configured to adhere very tightly when it placed over the first end with its much less smooth texture.

It is thought that the method and apparatus of the present invention will be understood from the above description and that it will be apparent that various changes may be made in the form, construct steps and arrangement of the parts and steps thereof without departing from the spirit and scope of the invention or sacrificing all of their material advantages. The form herein described is merely a preferred exemplary embodiment thereof.

I claim:

1. A method for protecting patient information on a label of a prescription medication container, comprising the steps of:
   providing a label having a first side and an opposing second side;
   said first side having a first zone which contains some information and a second zone which is free of any information;
   providing a panel which is configured to be relocated from a location above said second zone and placed over said first zone; and
   relocating said panel and covering from view said some information.

2. The method of claim 1 wherein: said panel is with an adhesive which is configured to adhere more strongly to a surface of said first zone than to a surface of said second zone.

3. The method of claim 2 wherein said adhesive is arranged on said panel so as to provide a removal facilitating region.

4. The method of claim 2 wherein said adhesive is configured in a first predetermined location adjacent to a solvent arranged in a second predetermined location.

5. The method of claim 2 wherein said adhesive is configured in a first predetermined location adjacent to a colorant material arranged in a second predetermined location.

6. The method of claim 5 wherein said colorant material is ink.

7. The method of claim 2 wherein said adhesive is arranged on a perimeter of an underside of said panel so as said perimeter is configured to adhere more strongly to a first zone perimeter.

8. The method of claim 1 further comprising the steps of:
   configuring said second zone with intentionally false information including a false patient name, false residential location, and prescription information.

9. The method of claim 8 further comprising the steps of configuring said second zone with a transparent smooth surface.

10. The method of claim 9 wherein a view side of each of said first zone and said second zone are made of a single piece of material and the intentionally false patient name and said false residential location are printed on said second zone and wherein said transparent smooth surface is applied above said intentionally false patient name.

11. A system for controlling the display of personal information on prescription labels on prescription containers, the system comprising:
   a base layer label configured to be adhered to a container;
   said base layer label having a first label portion having a first surface thereon which is configured to receive and retain thereon information;
   said base layer label having a second label portion having a second surface; and
   a removable portion adhered to said second surface so as to allow said removable portion to be peeled from said second surface with relative ease when compared to a level of effort involved in peeling said removable portion from said first surface after said removable portion has been relocated and adhered to said first surface.

12. The system of claim 11 wherein said removable portion is adhered to said second surface by a dual purpose adhesive and has a viewing side and an adhesion side, where said viewing side has a viewing surface which is configured to receive and retain thereon printed information.

13. The system of claim 12 wherein said dual purpose adhesive is positioned on said adhesion side in a predetermined pattern of lines having one of a solvent and a colorant.

14. The system of claim 11 wherein said second surface has fake information printed thereon which is uncovered when said removable portion is relocated.

15. A system for controlling the display of personal information on prescription labels on prescription containers, the system comprising:
   a base layer label configured to be securely adhered to a prescription container;
   said base layer label having a first label portion having a first surface thereon which is configured to receive and retain thereon printed information;
   said base layer label having a second label portion having a second surface which is smoother than said first surface;
   a removable portion adhered to said second surface by a dual purpose adhesive which is configured to allow said removable portion to be peeled from said second surface with relative ease when compared to a level of effort involved in peeling said removable portion from said first surface after said removable portion has been relocated and adhered to said first surface;
   said removable portion further having a viewing side and an adhesion side, where said viewing side has a viewing surface which is configured to receive and retain thereon printed information;
   said dual purpose adhesive further being positioned on said adhesion side in a predetermined pattern of lines having one of a solvent and a colorant; and
   said second surface further having fake information printed thereon which is uncovered when said removable portion is relocated.

* * * * *